US010155675B2

(12) United States Patent
Dubois et al.

(10) Patent No.: US 10,155,675 B2
(45) Date of Patent: Dec. 18, 2018

(54) METHOD FOR REMOVING GLYPHOSATE FROM A SOLUTION

(71) Applicant: International Business Machines Corporation, Armonk, NY (US)

(72) Inventors: Geraud J. Dubois, Los Altos, CA (US); Young-Hye Na, San Jose, CA (US); Lianna Samuel, Santa Clara, CA (US); Ran Wang, Sunnyvale, CA (US)

(73) Assignee: International Business Machines Corporation, Armonk, NY (US)

( * ) Notice: Subject to any disclaimer, the term of this patent is extended or adjusted under 35 U.S.C. 154(b) by 110 days.

(21) Appl. No.: 14/977,564

(22) Filed: Dec. 21, 2015

(65) Prior Publication Data

US 2017/0174534 A1    Jun. 22, 2017

(51) Int. Cl.
| | | |
|---|---|---|
| *C02F 1/28* | (2006.01) | |
| *C07F 9/44* | (2006.01) | |
| *B01D 15/26* | (2006.01) | |
| *C02F 101/30* | (2006.01) | |
| *C02F 101/34* | (2006.01) | |

(52) U.S. Cl.
CPC ............ *C02F 1/285* (2013.01); *B01D 15/265* (2013.01); *C07F 9/4465* (2013.01); *C02F 2101/306* (2013.01); *C02F 2101/34* (2013.01); *C02F 2305/08* (2013.01)

(58) Field of Classification Search
None
See application file for complete search history.

(56) References Cited

U.S. PATENT DOCUMENTS

| 6,616,846 | B2 | 9/2003 | Idziak et al. |
| 7,030,062 | B2* | 4/2006 | Nir ..................... A01N 25/08 |
| | | | 504/211 |
| 8,003,398 | B2 | 8/2011 | Bramble, Jr. et al. |
| 9,248,439 | B2* | 2/2016 | Hu ..................... B01J 35/026 |
| 2009/0114599 | A1* | 5/2009 | Nir ..................... B01J 20/12 |
| | | | 210/679 |
| 2009/0326293 | A1* | 12/2009 | Gomes ................ C07C 1/22 |
| | | | 585/324 |
| 2010/0267109 | A1* | 10/2010 | Rothberg .......... C12N 15/1006 |
| | | | 435/183 |

(Continued)

FOREIGN PATENT DOCUMENTS

| CN | 102079605 A | 6/2011 |
| CN | 104163486 A | 11/2014 |
| CN | 104163519 A | 11/2014 |

OTHER PUBLICATIONS

Milojevic-Rakic et al., "Polyaniline and its composites with zeolite ZSM-5 for efficient removal of glyphosate form aqueous solution," Journal of Microporous and Mesoporous Materials, vol. 180, Nov. 1, 2013, pp. 141-155.

(Continued)

*Primary Examiner* — Chester T Barry
(74) *Attorney, Agent, or Firm* — Shumaker & Sieffert, P.A.

(57) ABSTRACT

A method includes removing glyphosate from a solution by contacting the solution with a mesoporous inorganic particle having an average pore size of greater than zero and less than about 50 nm, wherein the mesoporous inorganic particle is functionalized with a positively charged moiety selected from ammonium, amine and combinations thereof.

12 Claims, 5 Drawing Sheets

(56) References Cited

U.S. PATENT DOCUMENTS

2011/0129537 A1* 6/2011 Vo-Dinh ............ A61K 41/0066
424/490
2013/0203602 A1* 8/2013 Riisager ................ A61K 9/143
504/358

OTHER PUBLICATIONS

Speth, "Glyphosate Removal From Drinking Water," Journal of Environmental Enginerring, vol. 119, No. 6, Nov./Dec. 1993, pp. 1139-1157.

* cited by examiner

METHOD FOR REMOVING GLYPHOSATE FROM A SOLUTION

BACKGROUND

Glyphosate, a type of organophosphate with the molecular structure shown below, has been widely used as a herbicide, and subsequently has entered into waterways and the drinking water supply:

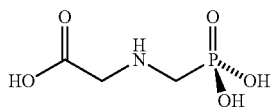

However, even at ultra-dilute concentrations (about 1 part per million (ppm) to about 1 part per billion (ppb)), glyphosate has been found to damage the environment. Since glyphosate has a low molecular weight, high solubility in water, and a relatively long half-life, removing ultra-dilute glyphosate from water using conventional filtration techniques can present challenges.

For example, current approaches for removing glyphosates include chlorination, ozonation, membrane filtration, UV irradiation and adsorption onto various materials, which can be employed either separately or in combination. However, these removal techniques are slow and can be relatively expensive.

UV irradiation and ozonation break down glyphosate to small molecules, and the extent to which this degradation is complete depends on both the length of contact time and initial concentration of the glyphosate. Incomplete molecular degradation from UV irradiation and ozonation can form smaller molecules (e.g., aminomethyl phosphonic acid), which can potentially be more damaging to the environment than glyphosate. Thus, to ensure full removal of the glyphosate and its byproducts, the contact time of the contaminated water and the UV or ozonation system should be on the order of hours, which makes these processes unacceptable for commercial processes with short production times.

Activated carbon is another frequently used method for water purification that can be ineffective in reliably removing glyphosate from water. While humic acids, clays and other natural materials can also be used for glyphosate removal, high salt concentrations in the water can reduce their efficiency. Humic acids, clays and other natural materials can also foul membranes used in purification processes.

SUMMARY

The present disclosure is directed to a method for quickly and effectively removing dilute glyphosate from a solution that is fast, easy to scale up, and can capture glyphosate without affecting other solutes in the solution.

In one aspect, the present disclosure is directed to a method including removing glyphosate from a solution by contacting the solution with a mesoporous inorganic particle having an average pore size of greater than zero and less than about 50 nm, wherein the mesoporous inorganic particle is functionalized with a positively charged moiety selected from ammonium, amine, and combinations thereof.

In another aspect, the present disclosure is directed to a method including removing glyphosate from an aqueous solution by contacting the aqueous solution with a mesoporous inorganic particle having the formula below, wherein the mesoporous inorganic particle is selected from the group consisting of silica, alumina, zeolite, and combinations thereof, wherein the inorganic mesoporous particle has an average central core particle diameter of less than about 200 nm and a pore size of greater than zero and less than about 5 nm, and wherein:

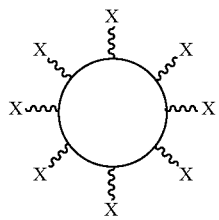

X = ammonium moiety or amines

〜〜 = L = alkyl, aryl, alkenyl the wavy lines represent linking groups on the particle, and the linking groups are selected from the group consisting of alkyl, aryl, alkenyl, and combinations thereof, and X represents positively charged functional groups on the linking groups, and wherein X is selected from ammonium, amine and combinations thereof.

In yet another embodiment, the present disclosure is directed to a filtration column, including: (i) a packing including a mesoporous inorganic particle selected from the group consisting of silica, alumina, zeolite, and combinations thereof, wherein the inorganic mesoporous particle has an average central core particle diameter of less than about 200 nm and a pore size of greater than zero and less than about 5 nm, and wherein the inorganic mesoporous particle has the formula below:

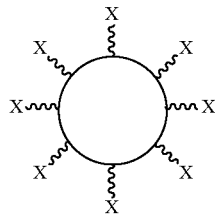

X = ammonium moiety or amines

〜〜 = L = alkyl, aryl, alkenyl wherein the wavy lines represent linking groups on the particle, and the linking groups are selected from the group consisting of alkyl, aryl, alkenyl, and combinations thereof, and X represents positively charged functional groups on the linking groups, and wherein X is an selected from ammonium, amine and combinations thereof; and (ii) an aqueous solution contacting the packing, wherein the aqueous solution includes less than about 5 ppm glyphosate.

In yet another embodiment, the present disclosure is directed to a filter including: (i) a mesoporous inorganic particle selected from the group consisting of silica, alumina, zeolite, and combinations thereof, wherein the inorganic mesoporous particle has an average central core particle diameter of less than about 200 nm and a pore size of greater than zero and less than about 5 nm, and wherein the inorganic mesoporous particle has the formula below:

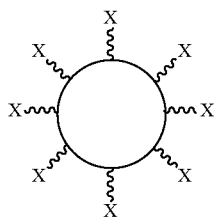

X = ammonium moiety or amines

~~~ = L = alkyl, aryl, alkenyl wherein the wavy lines represent linking groups on the particle, and the linking groups are selected from the group consisting of alkyl, aryl, alkenyl, and combinations thereof, and X represents positively charged functional groups on the linking groups, and wherein X is an selected from ammonium, amine and combinations thereof; and (ii) an aqueous solution contacting the filter, wherein the aqueous solution includes less than about 5 ppm glyphosate.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the figures indicate like elements.

DETAILED DESCRIPTION

Figure 1:
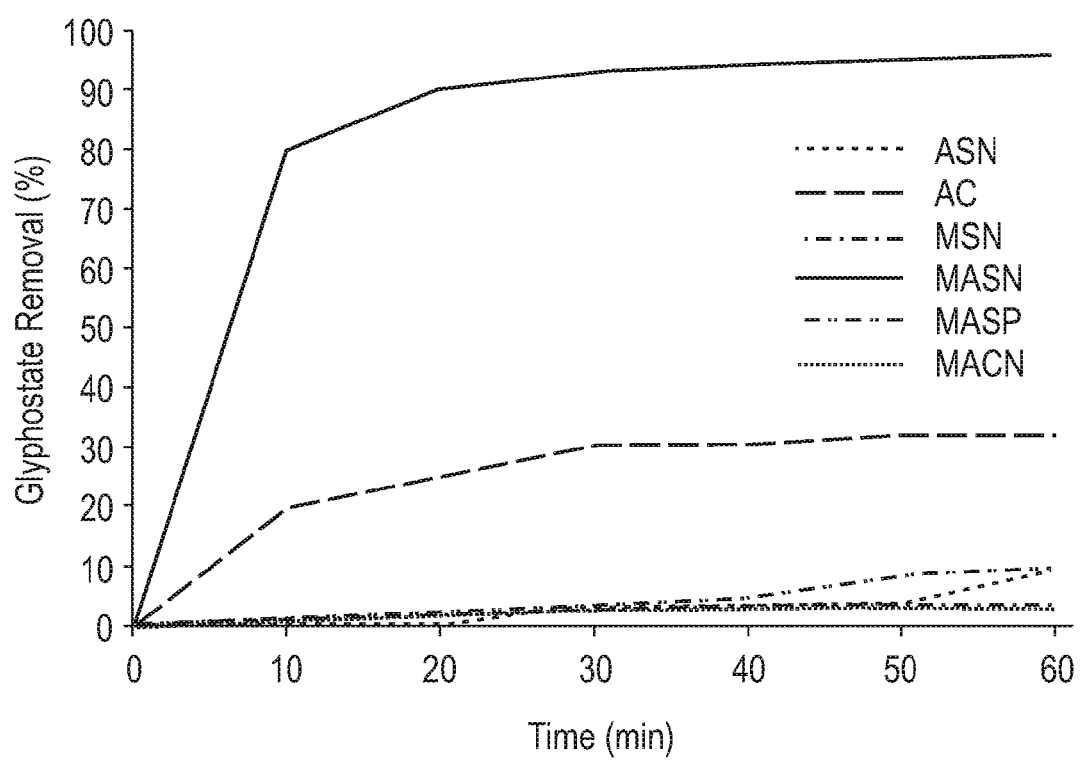
FIG. 1 is a plot showing treatment of a 5 ppm glyphosate solution by six types of adsorbents in the examples below.

The present disclosure is directed to a method for quick and efficient removal of glyphosate from an aqueous solution by contacting the aqueous solution with a filtration medium including a mesoporous inorganic particle functionalized with a positively charged moiety such as, for example, ammonium or amine.

In various embodiments, the mesoporous inorganic particle includes, but it not limited to, silica, alumina, zeolites, and combinations thereof. In various embodiments, the mesoporous inorganic particle is attached to a linking group such as, for example, alkyl, aryl, alkenyl and combinations thereof. The linking groups include a positively charged functional moiety such as, for example, ammonium, amine, and combinations thereof.

A schematic diagram of a non-limiting example of a suitable mesoporous particle for use in the filtration medium is shown in Formula I below:

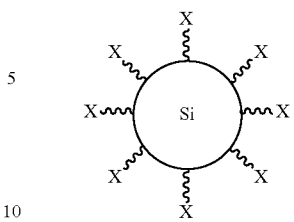

Formula I

In Formula I, which is not to scale, the central core particle has an average particle diameter of less than about 1 micron, or less than about 500 nm, or less than about 200 nm. In one embodiment, the central core particle is substantially spherical, although any shape particle may be used as long as the selected particle has a suitable pore size.

In various embodiments, the mesoporous inorganic particle has an average pore size of greater than about zero and less than about 50 nm, or about 1 nm to about 50 nm, or about 1 nm to about 30 nm, or about 1 nm to about 10 nm, or about 2 nm to about 5 nm, or about 3 nm to about 4 nm. In an example embodiment, which is not intended to be limiting, the pore size of the mesoporous inorganic particle can be measured by, for example, BET (Brunauer-Emmett-Teller) $N_2$-isotherm adsorption.

In various embodiments, which are not intended to be limiting, the surface area of the central core particle is about 800 $m^2$/g to about 1500 $m^2$/g, or about 1100 $m^2$/g to about 1200 $m^2$/g.

The mesoporous inorganic material of Formula I includes a linking group (represented by wavy lines in Formula I) attached to the central mesoporous inorganic particle such as, for example, alkyl, aryl, alkenyl, and combinations thereof. In some embodiments, the linking group is an alkyl group.

A positively charged functional group X such as, for example, an ammonium moiety, an amine moiety, and combinations thereof, is attached to the linking groups. The point of attachment can be along the backbone of the linking group or at a terminus. In various embodiments, the functional group X is selected from primary amines, secondary amines, tertiary amines, and quaternary ammonium moieties.

A wide variety of glyphosate-containing solutions can be processed by a filtration medium including the inorganic mesoporous material. In various embodiments, the solutions can have dilute concentrations of glyphosate such as, for example, from about 5 parts per billion (ppb) to 1000 parts per million (ppm). In various embodiments, the solutions can include any aqueous or organic solvent, or combinations thereof, that can dissolve glyphosates, although aqueous solutions are preferred. In various embodiments, the solution can have a wide range of pH values from about 1 to about 11, or about 3 to about 10.

As a non-limiting example, in processing environments where the pH of the aqueous solution contacting the inorganic mesoporous material is substantially neutral (a pH of about 6 to about 8, or a pH of about 7), the first phosphonic proton and the carboxylate proton from glyphosate are fully dissociated. The positively charged mesoporous inorganic material can efficiently adsorb the glyphosate by electrostatic interaction, and the extremely high surface area of the central core mesoporous inorganic particle and large number of positively charged functional groups on the particle efficiently remove glyphosate within a short period of time.

The inorganic mesoporous material can be contacted with the glyphosate-containing solution in a wide variety of ways such as, for example, allowing the solution to migrate through a layer of packing in a column including a granular bed incorporating the inorganic mesoporous material. In such a column, the packing can optionally include other fillers such as, for example, non-functionalized inorganic particles, diatomaceous earth, cellulose, perlite, and the like.

In another embodiment, the inorganic mesoporous material is incorporated in a filter construction to adsorb glyphosate as the glyphosate-containing solution moves through the filter.

In another embodiment, the glyphosate-containing solution can simply be stirred together with the inorganic mesoporous material for a time sufficient to ensure contact between the glyphosate and the positively charged functional groups on the mesoporous material, and the inorganic mesoporous material subsequently removed by a later filtration step. In various embodiments, which are not intended to be limiting, the stirring time can be about 1 minute to about 1 hour. A complex including the mesoporous material and adsorbed glyphosate, as well as residual mesoporous material, can subsequently be removed by an additional filtration step such as, for example, sand filtration, microfiltration, ultrafiltration, and combinations thereof.

The pressure or temperature for the solution can vary widely depending on the type of filter used in the process. For example, the operational pressure using ultrafiltration is about 30 to about 70 pounds per square inch (psi), and microfiltration is typically less than about 30 psi. Operational temperature can vary depending on the stability of functionalized nanoparticles. For example, mild heat conditions (greater than about 20° C. and less than about 50° C.) or room temperatures are preferred for amine-functionalized silica nanoparticles in which the functional groups are attached to the particle surfaces through a silane coupling reaction.

Embodiments of the invention will now be described with reference to the following non-limiting examples.

EXAMPLES

Six types of adsorbents as shown in Table 1 below were tested to adsorb ultra-dilute glyphosate from water. The tested adsorbents included different charged functional groups, particle diameters and pore sizes, included activated carbon (AC), amine functionalized silica particles (MASP) and silica nanoparticles (mesoporous silica nanoparticles (MSN), mesoporous amine functionalized silica nanoparticles (MASN), mesoporous carboxylic functionalized silica nanoparticles (MCSN), amine functionalized silica nanoparticles (ASN)).

TABLE 1

| Adsorbent | Particle Diameter | Pore Size (nm) |
| --- | --- | --- |
| Activated carbon (AC) | 100 mesh | N.A. |
| Mesoporous silica nanoparticles (MSN) | 200 nm | 4 |
| Mesoporous amine functionalized silica nanoparticles (MASN) | 200 nm | 4 |
| Mesoporous carboxylic functionalized silica nanoparticles (MCSN) | 200 nm | 4 |
| Amine functionalized silica nanoparticles (ASN) | 100 nm | no |
| Amine functionalized silica particles (MASP) | 40 μm | 6~7 |

Materials

The adsorbate used in this experiment was analytical grade glyphosate obtained from Sigma-Aldrich, Wisconsin, USA, under the trade designation Pestanal. 0.01 grams of glyphosate was dissolved in 1 liter of deionized water, to create a stock solution (~10 ppm). All other initial concentrations utilized herein were made by diluting the stock solution with deionized water.

The adsorbents tested were activated carbon from Sigma-Aldrich, silica from Sigma-Aldrich, propylamine functionalized silica from Sigma-Aldrich, 3-aminopropyl functionalized nanosilica from Sigma Aldrich, and propylamine functionalized silica from SiliCycle, Quebec, Canada. The central core particle diameter and pore size of the adsorbents are shown in Table 1.

General Procedure of Solution Preparation and Characterization

Glyphosate solution having an initial concentration (5 ppm) was used to determine the adsorption efficiency of the adsorbents. Further dilution was done to prepare solution of 2 ppm and 500 ppb.

The vials were then sealed and the mixtures stirred for predetermined time intervals, up to 1.5 hours. After each time interval, the mixture was filtered to remove the adsorbents and any captured glyphosate.

The concentration of glyphosate was then measured using inductively coupled plasma spectrometer available from Thermo Scientific under the trade designation IC AP 6300 Duo View Spectrometer. The spectrometer had a solid state CID detector and a detection limit of 2 ppb for phosphorous (P) in deionized water. The amount of adsorption, $q_t$ (mg/g) at each time was determined by the following equation:

$$q_t = (C_0 - C_t)V/W$$

where $C_0$ is the initial concentration of glyphosate, $C_t$ is the glyphosate concentration after a certain period of time, t, V is the volume of solution and NV is the weight of adsorbent used. Final adsorption efficiencies were used to determine which adsorbent is most effective in removing glyphosate.

Example 1: Glyphosate Removal Test by Mesoporous Amine Functionalized Silica Nanoparticles (MASN)

As shown in the plot of FIG. 1, the star-shaped block copolymer MASN showed an outstanding glyphosate removal rate. 97% glyphosate in the ultra-diluted solution (5 ppm) was successfully removed. The removal rate was much higher than those of the activated carbon (32%) and the rest of particles (less than 10%). While not wishing to be bound by any theory, presently available evidence indicates that this efficiency can be attributed to the high surface area of MASN, the highly dense amine groups on the central core particle, and the suitable pore size for the central core particle.

Example 2: Glyphosate Removal Test by Activated Carbon (AC)

Activated carbon has a large surface area and a low price, and is one of the most widely used adsorbents. However, the negative surface charge of AC (−20 mV) limits its application for glyphosate removal. As shown in FIG. 1, the removal rate is only about 32%.

Example 3: Glyphosate Removal Test by Mesoporous Silica Nanoparticles (MSN)

Even though MSN has a particle diameter and pore size similar to MASN, the lack of amine functional groups made MSN less able to efficiently adsorb glyphosate (<10% removal rate in FIG. 1).

Example 4: Glyphosate Removal Test by Mesoporous Carboxylic Functionalized Silica Nanoparticles (MCSN)

MSCN has a particle diameter and pore size similar to that of MASN, but MSCN has the same negative charge as glyphosate, which makes MSCN less able to efficiently adsorb glyphosate (<10% removal rate in FIG. 1).

Example 5: Glyphosate Removal Test by Amine Functionalized Silica Nanoparticles (ASN)

ASN has the same type of amine groups on the particle as MASN, but ASN lacks a suitable pore structure to capture glyphosate. As shown in FIG. 1, the removal rate of ASN is less than 10%.

Example 6: Glyphosate Removal Test by Amine Functionalized Silica Particles (MASP)

MASP has the same type of amine groups on the particle as MASN, but MASP has a smaller particle diameter and smaller surface area, and lacks the porous structure needed to efficiently capture glyphosate. As a result, the removal rate of MASP is less than about 10% (FIG. 1).

The removal result (FIG. 1) clearly showed four of the six types of adsorbents failed in the removal test by removing less than 10% glyphosate from water after one hour. On the other hand, AC and MASN exhibited good adsorption capacity. Between these two candidates, MASN had a much faster adsorption rate than AC, which is usually selected as a commercial adsorbent, and also a much higher removal rate (97%) compared with that of AC (32%) in one hour.

While not wishing to be bound by any theory, presently available evidence indicates that the removal efficiency of MASN can be attributed to its high surface area and the large number of positively charged amine groups on the central core particle.

MSN, MASN and MCSN have the same central core particle diameter (200 nm) and the same pore size (4 nm), but the different charge from the different functional groups on the nanoparticle surface shows that only MASN with its amine functional groups (ammonium group in water at pH 7) could effectively adsorb glyphosate under testing conditions.

MASN, ASN and MASP share the same positive charge with amine functional groups modified on the particle surface, but ASN is less able to remove glyphosate without the desired mesoporous structure, In all, MASN is the best adsorbent (97% removal) from the six candidates with the proper combination of charge, surface area and pore size.

Example 7: Glyphosate Removal Test by MASN and AC at 2 ppm and 500 ppb

Glyphosate solutions with initial concentrations of 2 ppm and 500 ppb were used to determine the adsorption efficiency of MASN and AC. As discussed above, a more dilute solution will lead to less adsorption.

As shown in Table 2, at the 2 ppm level, MASN can remove 86% glyphosate, while AC can remove 30%. At the 500 ppb level, MASN is still able to remove 60% glyphosate, while AC can only remove 10%. So, even for a solution having glyphosate at a ppb level, MASN was still an outstanding adsorbent.

TABLE 2

| Glyphosate concentration in water | Glyphosate removal by MASN | Glyphosate removal by AC |
|---|---|---|
| 5 ppm | 97% | 32% |
| 2 ppm | 86% | 30% |
| 500 ppb | 60% | 10% |

Example 8: Kinetic Study of Glyphosate Removal

A glyphosate solution with an initial concentration of 5 ppm was used to study the kinetics of glyphosate removal by MASN and activated carbon. Glyphosate removal by AC was also performed as a benchmark.

The adsorption kinetics associated with the glyphosate removal for each adsorbent were compared to the Lagergren and pseudo-second order kinetic equations. The first equation used to describe the adsorption of an adsorbate from aqueous solution is Lagergren's kinetic equation. This equation assumes adsorption of the adsorbate onto the adsorbent at a rate given by:

$$dq_t/dt = k_1(q_e - q_t)$$

where $q_e$ and $q_t$ are the adsorption capacities at equilibrium and at time t, respectively, and $k_1$ is the rate constant of a pseudo-first order adsorption process. Given that at time t=0 $q_t$=0 and at time t=t $q_t$=$q_t$, the above equation can be integrated between the boundaries of t=0 and t=t, to give the following equation:

$$q_t = q_e(1 - e^{-kt})$$

which can be linearized into the Legergren equation:

$$\log(q_e - q_t) = \log(g_m) - k_1 t/2.303$$

Thus the rate constant can be determined by plotting vs t.

In pseudo-second order adsorption kinetics, we assumed that the adsorbate gets adsorbed onto two surface sites and is represented by the equation:

$$dq_t/dt = k_2(q_e - q_t)^2$$

where $k_2$ is the rate of second-order adsorption (g/mg min). This equation can be separated, and then integrating to the same limits as before, gives:

$$1/(q_e - q_t) = 1/q_e + k_2 t$$

While this equation can be linearized into five different forms, the most widely accepted form was used in this study:

$$t/q_t = 1/(k_2 q_e^2) + t/q_e$$

From this equation $k_2$ can be found from plotting $t/q_t$ vs t.

The adsorption kinetics may be described by a simple first order reaction, in which the reaction rate depends on the concentration of only one reactant, or a pseudo second order equation, in which the reaction rate mainly depends on the concentration of two reactants.

Figure 2A:
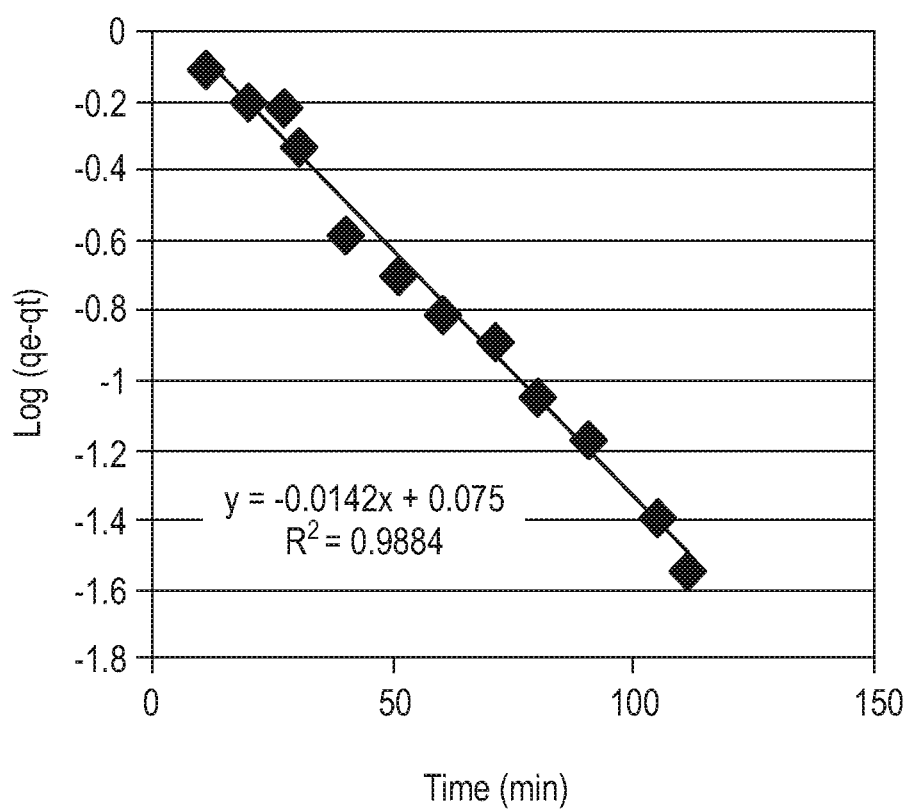
FIG. 2A is a plot of a kinetic study of glyphosate removal by MASN with a first-order model.
Figure 2B:
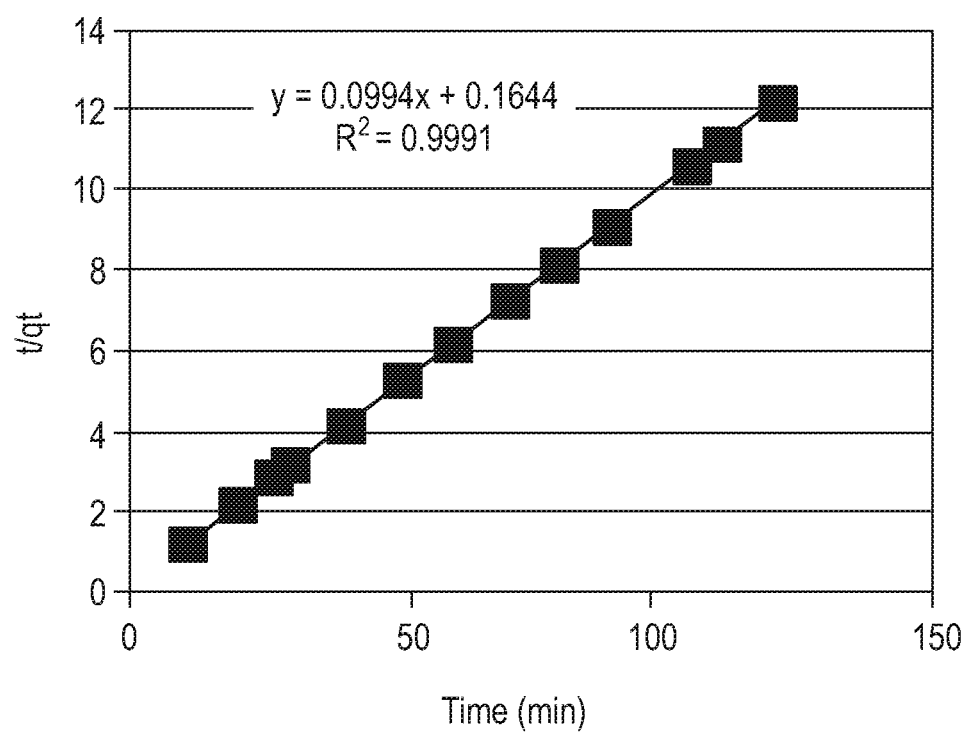
FIG. 2B is a plot of a kinetic study of glyphosate removal by MASN with a second-order model.

As indicated in FIGS. 2A and 2B, the simulate correlation factor based on first order reaction is only 0.9851, far from a good correlation. On the contrary, the second order modeling gave a very good fit with a good correlation factor, 0.9991. As shown in FIG. 2B, glyphosate removal by MASN better fits a second order adsorption reaction model.

Figure 3A:
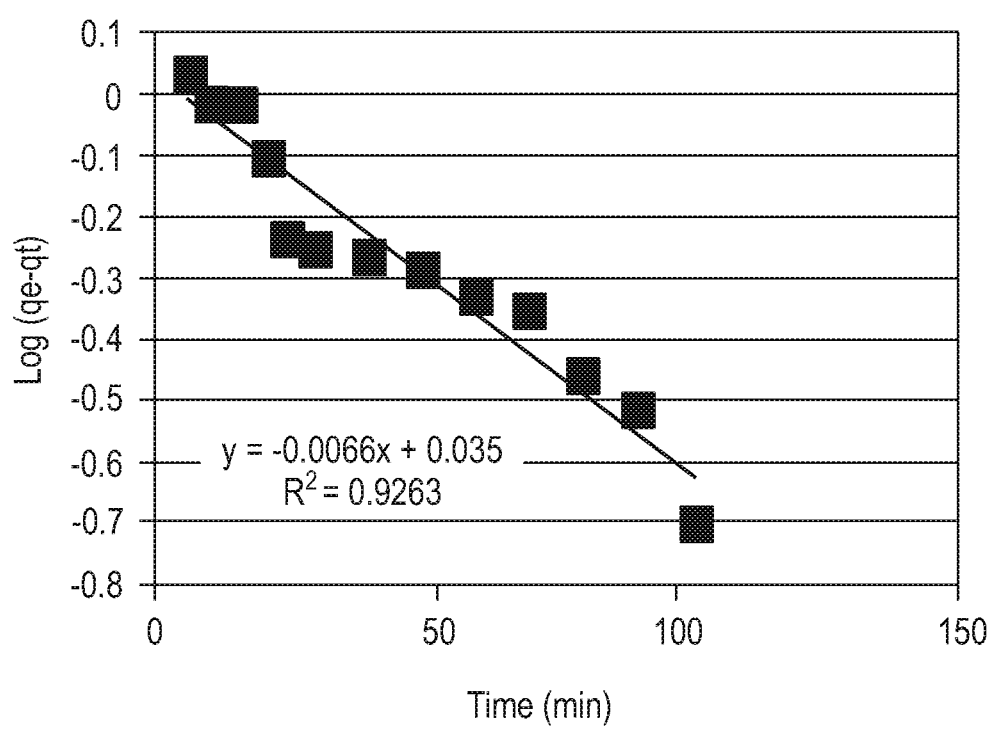
FIG. 3A is a plot of a kinetic study of glyphosate removal by activated carbon (AC) with a first-order model.
Figure 3B:
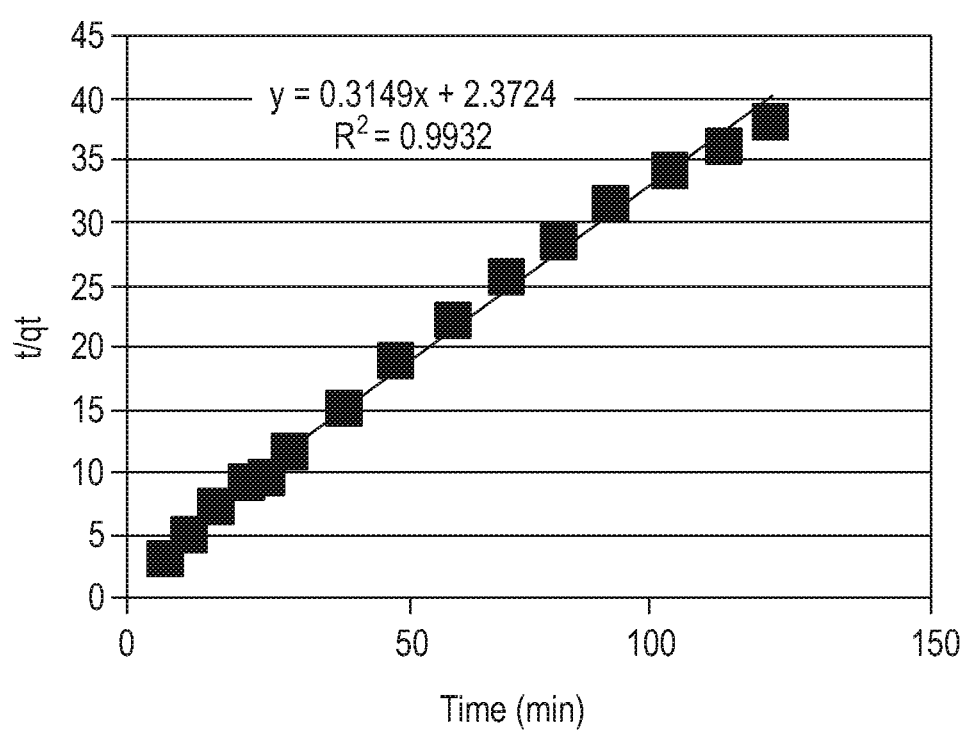
FIG. 3B is a plot of a kinetic study of glyphosate removal by AC with a second-order model.

As indicated in FIGS. 3A and 3B, the glyphosate removal by AC also better fits a second-order reaction model (FIG. 3B) than a first order reaction model (FIG. 3A) (R-square 0.9932 vs. 0.9263).

Table 3 summarizes the kinetic study of glyphosate removal by MASN and AC under first order reaction simulations and second order reaction simulations. The results clearly show that MASN and AC most closely fit a second order reaction model.

Under a second order simulation, glyphosate removal by MASN has a reaction rate constant ($k_2$) that is seven times greater than AC, which means that MASN can remove glyphosate from water much faster than AC under the same conditions. Moreover, MASN shows an adsorption at equilibrium ($q_e$) that is three times greater than AC, and the calculated results are quite consistent with the experimental data shown in Examples 1-7 above, such as $q_e$ test (MASN)=9.6 mg/g and $q_e$ second-order (MASN)=10.06 mg/g, and $q_e$ test (AC)=3.2 mg/g and $q_e$ second-order (AC)=3.18 mg/g.

TABLE 3

| Adsorbent | $C_0$ (ppm) | $q_e$ test (mg/g) | First order | | | Second order | | |
| --- | --- | --- | --- | --- | --- | --- | --- | --- |
| | | | $k_1$ (min$^{-1}$) | $q_e$ (mg/g) | $R^2$ | $k_2$ (g/mg/min) | $q_e$ (mg/g) | $R^2$ |
| AC | 5 | 3.2 | 0.015 | 1.04 | 0.9263 | 0.042 | 3.18 | 0.9932 |
| MASN | 5 | 9.6 | 0.304 | 1.07 | 0.9851 | 0.282 | 10.06 | 0.9991 |

As mentioned above, the second order reaction rate mainly depends on the concentration of two reactants and the reaction rate (k). Since one reactant, glyphosate, has an ultra-low concentration at the ppm~ppb level, normal adsorbents have difficulty efficiently removing glyphosate. MASN has a highly positive charge, a large surface area, and a small pore size, which can provide highly efficient glyphosate removal.

Various embodiments of the invention have been described. These and other embodiments are within the scope of the following claims.

The invention claimed is:

1. A method comprising removing glyphosate from a solution by contacting the solution with a mesoporous inorganic particle selected from the group consisting of silica, alumina, zeolite, and combinations thereof, wherein the inorganic particle has an average pore size of about 1 nm to about 5 nm, wherein the mesoporous inorganic particle is functionalized with a positively charged moiety selected from ammonium, a primary amine and combinations thereof.

2. The method of claim 1, wherein the mesoporous inorganic particle comprises silica.

3. The method of claim 1, wherein the mesoporous inorganic particle is functionalized with a primary amine.

4. The method of claim 1, wherein the aqueous solution comprises less than about 5 ppm glyphosate.

5. The method of claim 1, wherein the aqueous solution comprises less than about 2 ppm glyphosate.

6. The method of claim 1, wherein the aqueous solution comprises less than about 500 ppb glyphosate.

7. The method of claim 1, wherein the mesoporous inorganic particle comprises a central core with an average particle diameter of less than about 1 micron.

8. The method of claim 1, wherein the particle is a silica particle with the following chemical structure:

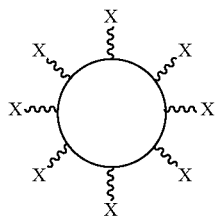

X = ammonium moiety or amines

〰️ = L = alkyl, aryl, alkenyl wherein the wavy lines represent linking groups on the particle, and the linking groups are selected from the group consisting of alkyl, aryl, alkenyl, and combinations thereof, and X represents functional groups on the linking groups, wherein X is selected from ammonium, primary amine and combinations thereof.

9. The method of claim 8, wherein the silica particle has a pore size of greater than zero and less than about 5 nm.

10. The method of claim 8, wherein the silica particle has an average particle diameter of about 200 nm.

11. The method of claim 8, wherein the solution comprises water.

12. A method comprising removing glyphosate from an aqueous solution by contacting the aqueous solution with a mesoporous inorganic particle having the structure below, wherein the mesoporous inorganic particle is selected from the group consisting of silica, alumina, zeolite, and combinations thereof, wherein the inorganic mesoporous particle has an average central core particle diameter of about 200 nm and a pore size of greater than zero and less than about 5 nm, and wherein:

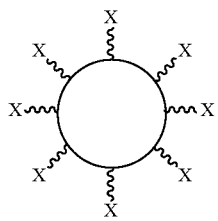

X = ammonium moiety or amines

〰️ = L = alkyl, aryl, alkenyl the wavy lines represent linking groups on the particle, and the linking groups are alkyl, and X represents positively charged functional groups on the linking groups, and wherein X is selected from ammonium, primary amine and combinations thereof.

* * * * *